US00PP18139P3

(12) United States Plant Patent

Iezzoni et al.

(10) Patent No.: US PP18,139 P3

(45) Date of Patent: Oct. 23, 2007

(54) PEACH TREE NAMED 'MSUP8706'

(50) Latin Name: *Prunus persica*
Varietal Denomination: MSUP8706

(75) Inventors: Amy Iezzoni, Okemos, MI (US); William Shane, Niles, MI (US)

(73) Assignee: Michigan State University, East Lansing, MI (US)

( * ) Notice: Subject to any disclaimer, the term of this patent is extended or adjusted under 35 U.S.C. 154(b) by 18 days.

(21) Appl. No.: 11/273,006

(22) Filed: Nov. 14, 2005

(65) Prior Publication Data

US 2007/0113310 P1 May 17, 2007

(51) Int. Cl.
*A01H 5/00* (2006.01)

(52) U.S. Cl. ..... Plt./198

(58) Field of Classification Search ..... Plt./198, Plt./194

See application file for complete search history.

*Primary Examiner*—Kent Bell
*Assistant Examiner*—Annette H Para
(74) *Attorney, Agent, or Firm*—Flynn, Thiel, Boutell & Tanis, P.C.

(57) ABSTRACT

A new peach variety, *Prunus persica,* (hereinafter referred to as the MSUP8706 peach variety), which was developed by Amy Iezzoni and Bill Shane in a breeding program at the Southwest Michigan Research and Extension Center in Benton Harbor, Mich., having the following number of unique and desirable features:

1. A fruit with excellent shipping and storage characteristics.
2. A fruit maturing at the same season as the Loring peach (an unpatented selection).
3. A generally round fruit with freestone, yellow flesh, and an attractive red blush.

3 Drawing Sheets

*Prunus persica* 'MSUP8706'.

FIELD OF THE INVENTION

The new variety of MSUP8706 peach tree was developed by Amy Iezzoni and William Shane in a peach breeding program. The MSUP8706 peach was developed as a cross between SH424 (unpatented), an experimental selection from Michigan State University and Fayette, an unpatented selection. The parent tree was grown at Clarksville, Mich. and was tested as MSU Plot II, Row 7, Tree 26. MSUP8706 is an interspecific cross.

This new and distinct variety of peach tree has been asexually propagated by budding on Halford peach seedling rootstock in Benton Harbor, Mich. The asexual propagation demonstrates that such reproduction of the characteristics of the tree is consistent and is established and transmitted through succeeding generations.

BRIEF DESCRIPTION OF THE DRAWINGS

The accompanying photographs show typical specimens of the new variety as depicted in color as nearly true as is reasonably possible in color illustrations of this character. These specimens were obtained at Benton Harbor, Berrien County, Mich.

FIG. 1/3 depicts the fruit of the new variety.

FIG. 2/3 depicts the blossoms of the new variety.

FIG. 3/3 depicts the leaves of the new variety.

DETAILED DESCRIPTION OF THE VARIETY

The following description of the fruit and foliage of the new variety is based on observations of specimens grown in Berrien County of southwestern Michigan. The color terminology is in accordance with The Royal Horticultural Society Colour Chart, published by The Royal Horticultural Society of London, England.

Tree:

*Age of specimen.*—10 years old.
*Height.*—11 feet.
*Width.*—8 feet.
*Size.*—Medium.
*Vigor.*—Vigorous, requires annual pruning.
*Density.*—Medium, internode length 22 to 52 mm.
*Form.*—Spreading, does not require supplemental support.
*Production.*—Productive, generally ripens in two or three pickings.
*Bearing.*—Annual, harvest season lasts 4 to 6 days in normal year.
*Disease resistance.*—Moderate resistance to bacterial spot.
*Cold hardiness.*—Very hardy.

Trunk:

*Size.*—Medium, averaging 82 cm at 100 cm above ground level.
*Surface.*—Medium shaggy, color 201C.
*Lenticels.*—Large, averaging 0.5 mm in width and 3 mm in length, color 198D, density 1.8/cm$^2$, surface slightly rough.

Branches: Approximate branch crotch angle: 30 degrees from the horizontal.

*1 year old branches.*—Surface smooth, color ranging from greyed purple RHS 184B to RHS greyed-red 181B with some RHS yellow-green 152C highlights, especially on smaller diameter limbs, slightly shiny; length 40 to 65 cm; 6–9 mm diameter at base to 4 mm at apical end, smooth; lenticels conspicuous at basal end.

*2 year old branches.*—Color RHS Grey, brown 199 A to RHS Greyed, red 181 B, nearly smooth with conspicuous, abundant lenticels with density of 10 per 1 square cm, slightly raised cream white lenticels, limb diameter 7 to 13 mm.

*3 year old branches.*—Color RHS Greyed-orange 165B with slight olive overtones, surface with slightly raised cream white lenticels, 2 mm horizontal length, slight vertical striations, diameter 12 mm to 18 mm.

Leaves:

*Size.*—204 mm×47 mm.
*Color.*—41B.
*Form.*—Lanceolate, pointed.
*Thickness.*—Medium.
*Texture.*—Medium crisp.
*Margin.*—Crenate.
*Petiole.*—11 mm, color 151A.
*Glands.*—4–5, globose on petiole and leaf base, color 171A.
*Stipules.*—Absent.

Flower buds:

*Size.*—Length 10 to 13 mm, width 6 to 8 mm, color 73B.

Flowers:

*Blooming period.*—April 25 to May 5 in Benton Harbor, Mich.
*Presentation.*—Non-showy.
*Petals.*—Number 5, cupped, length 5 mm, color 73B.
*Stamens.*—Anthers slightly curved at end, filament length 13 to 15 mm, color 73A.
*Pistil.*—Length 10 mm, color 162 C.
*Sepal.*—Number 10, length 5 mm, color 60B.

Fruit:

*Maturity when described.*—Firm ripe.
*Date of first picking.*—August 15 in Southwestern Michigan.
*Size.*—Transverse diameter, 65 to 78 mm.
*Form.*—Round, slightly oblate.
*Suture.*—Slightly indented, well knitted.
*Pistil point.*—Usually indented to slightly extended.
*Cavity.*—Average depth 36 mm, average breadth 26 mm.

Skin:

*Thickness.*—Medium.
*Texture.*—Smooth.
*Tendency to crack.*—None.
*Down.*—Moderate.
*Color.*—Attractive 80% red 47B blush with slight stripe over a background of yellow-orange 21C when ripe.

Flesh:

*Texture.*—Firm, melting when fully ripe and beyond.
*Aroma.*—Sweet, aromatic.
*Brix.*—Average 11.36.
*Fibers.*—Inconspicuous when eating.
*Color.*—Yellow-orange 23C.
*Coloration at the pit.*—Yellow 23C with some red 40B bleeding from the pit onto adjacent flesh.
*Eating quality.*—Excellent, moderate acidity, sweet.

Stone:

*Size.*—Length 34 mm, width 25 mm, thickness 17 mm.
*Form.*—Obovate.
*Kernel.*—BTH, not edible, germination after stratification.
*Apex.*—Pointed, slightly asymmetrical.
*Sides.*—Slightly unequal.
*Base.*—Narrow.
*Surface.*—Combination of etched and honeycombed.
*Color.*—Red 46A drying to 166A.
*Type.*—Freestone.
*Tendency to crack.*—None to very slight.

Use: Fresh market.

Shipping quality: Excellent, can be graded on a commercial peach grader and shipped via truck.

Keeping quality: Excellent, will store for up to 2 months in common storage with minimal loss of flavor and color.

I claim:

1. A new and distinct variety of peach tree, *Prunus persica,* substantially as herein shown and described, characterized particularly as to novelty by the unique combination of vigorous, regular bearing tree producing round, freestone fruits with excellent shipping and storage characteristics having with 80% blushed red skin color at maturity which occurs 15 days after the maturity of 'Redhaven' (an unpatented selection).

* * * * *

FIG. 1, 'A Peach Tree Named MSUP8706', Iezzoni et al,
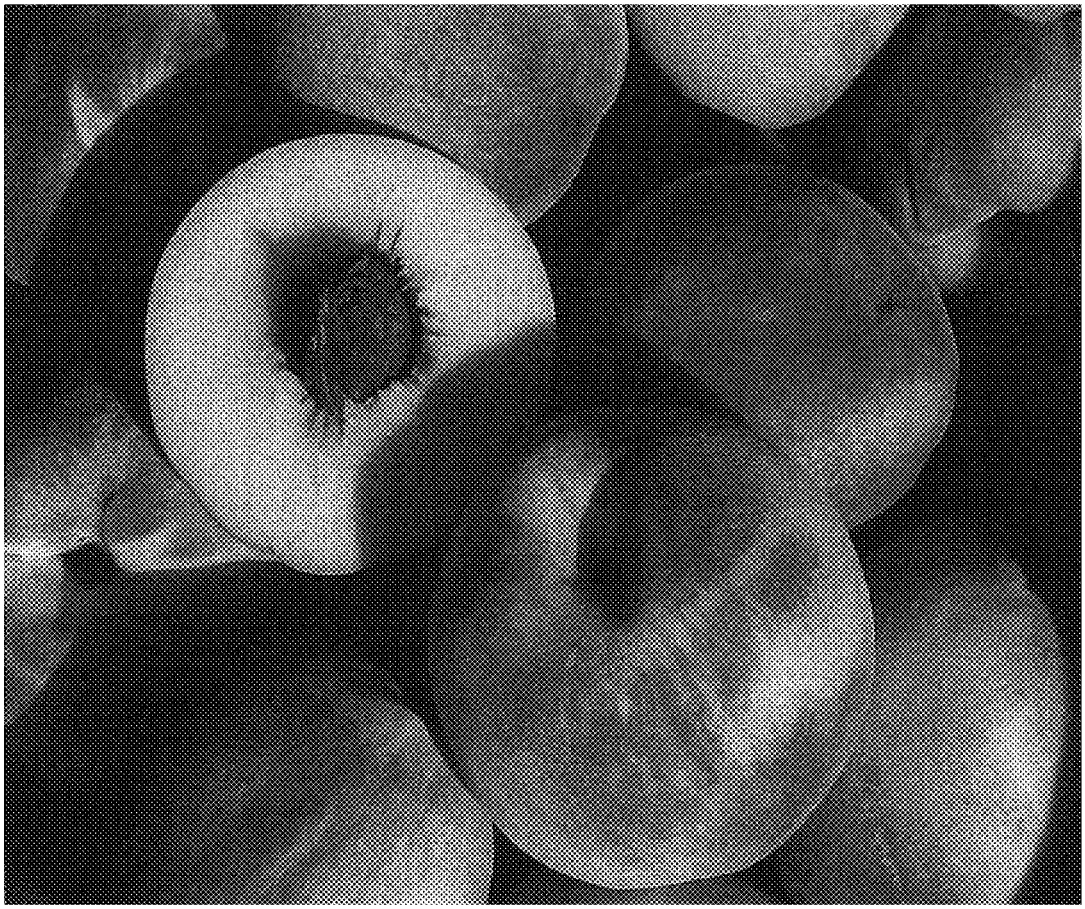

FIG. 2, 'A Peach Tree Named MSUP8706', Iezzoni et al,
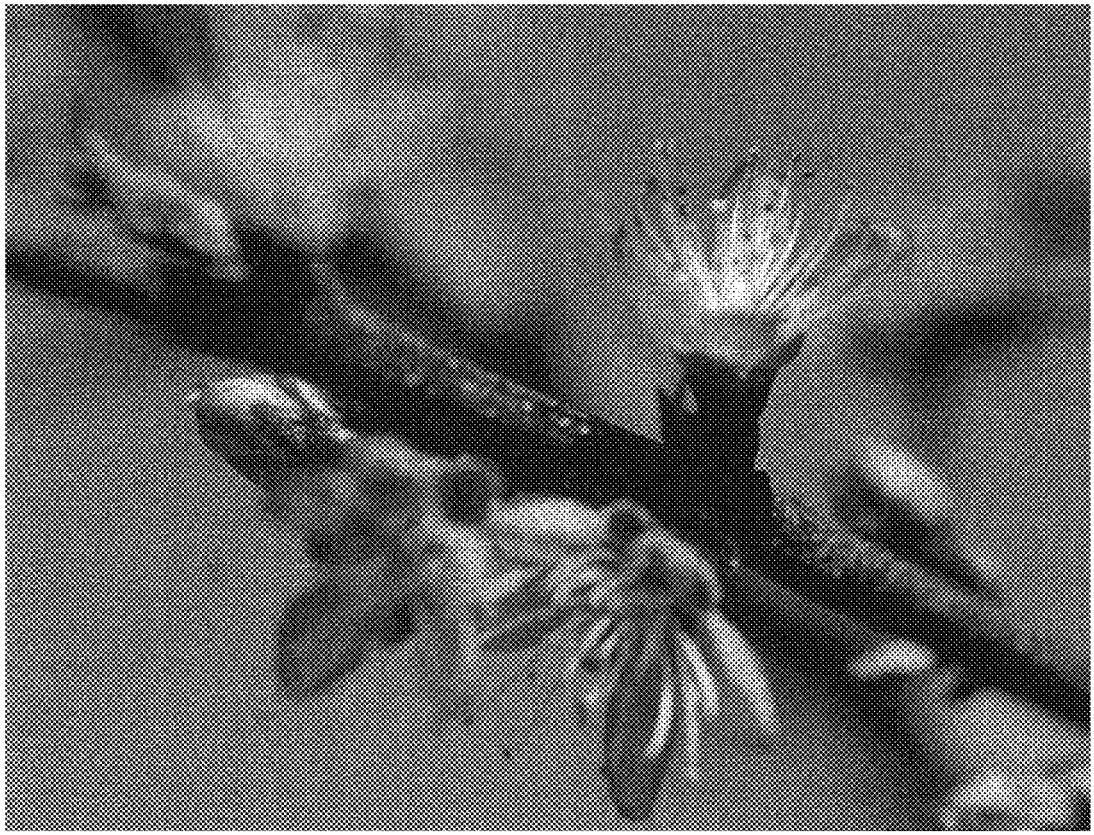

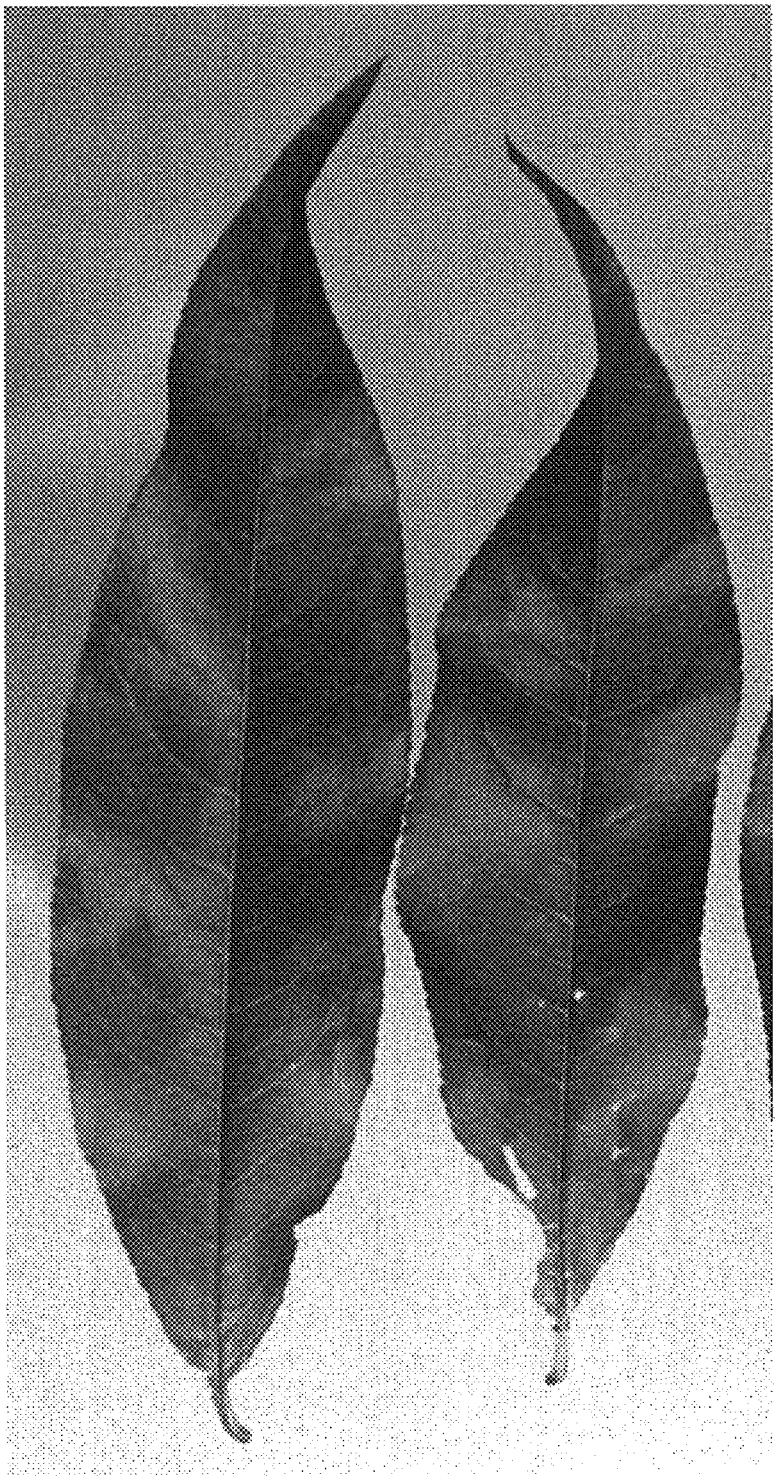

FIG. 3, 'A Peach Tree Named MSUP8706', Iezzoni et al,